(12) United States Patent
Schneider et al.

(10) Patent No.: US 7,998,327 B2
(45) Date of Patent: Aug. 16, 2011

(54) MEASURING SENSOR

(75) Inventors: Jens Schneider, Rodez-Cedex (FR); Detlef Heimann, Gerlingen (DE); Thomas Wahl, Pforzheim (DE); James-Richard Waldrop, II, Belton, SC (US)

(73) Assignee: Robert Bosch GmbH, Stuttgart (DE)

( * ) Notice: Subject to any disclaimer, the term of this patent is extended or adjusted under 35 U.S.C. 154(b) by 986 days.

(21) Appl. No.: 10/540,652

(22) PCT Filed: Nov. 17, 2003

(86) PCT No.: PCT/DE03/03799
§ 371 (c)(1), (2), (4) Date: Apr. 17, 2006

(87) PCT Pub. No.: WO2004/061445
PCT Pub. Date: Jul. 22, 2004

(65) Prior Publication Data
US 2006/0226009 A1 Oct. 12, 2006

(30) Foreign Application Priority Data
Dec. 23, 2002 (DE) .................................. 102 60 849

(51) Int. Cl.
*G01N 27/409* (2006.01)
*G01N 27/26* (2006.01)
(52) U.S. Cl. ......... 204/429; 204/424; 204/427; 204/428
(58) Field of Classification Search .................... 204/429
See application file for complete search history.

(56) References Cited

U.S. PATENT DOCUMENTS

| | | | | |
|---|---|---|---|---|
| 4,296,148 A * | 10/1981 | Friese | ............................. | 427/125 |
| 4,402,820 A * | 9/1983 | Sano et al. | ..................... | 204/425 |
| 5,271,821 A * | 12/1993 | Ogasawara et al. | ........... | 204/429 |
| 5,368,713 A * | 11/1994 | Friese et al. | ................... | 204/429 |
| 5,486,279 A * | 1/1996 | Friese et al. | ................... | 204/429 |
| 6,537,431 B1* | 3/2003 | Tatsumoto et al. | ........... | 204/426 |
| 6,630,062 B1 | 10/2003 | Anderson et al. | | |
| 2002/0060152 A1* | 5/2002 | Hotta et al. | ..................... | 204/429 |
| 2002/0102347 A1 | 8/2002 | Clyde et al. | | |
| 2003/0205468 A1* | 11/2003 | Wu et al. | ........................ | 204/428 |
| 2003/0230484 A1* | 12/2003 | Jain et al. | ....................... | 204/424 |
| 2004/0007462 A1* | 1/2004 | Hotta et al. | .................... | 204/429 |
| 2004/0117974 A1* | 6/2004 | Clyde et al. | .................. | 29/592.1 |

FOREIGN PATENT DOCUMENTS

| | | |
|---|---|---|
| DE | 43 33 898 | 4/1995 |
| DE | 197 41 203 | 3/1998 |
| DE | 199 41 051 | 3/2001 |

(Continued)

*Primary Examiner* — Harry D Wilkins, III
*Assistant Examiner* — Bryan D. Ripa
(74) *Attorney, Agent, or Firm* — Kenyon & Kenyon LLP

(57) ABSTRACT

A measuring sensor is described for determining a physical property of a measured gas, especially for determining the oxygen concentration or the pollutant concentration in the exhaust gas of internal combustion engines, which has a sensor element that is exposable to the measured gas which is at least partially coated with a protective layer that protects against harmful components in the measured gas. In order to achieve producing a "contamination protection", that is cost-effective from a manufacturing technology point of view, particularly against silicon compounds and phosphorus compounds, the protective layer (26) is made of highly active γ- or δ-aluminum oxide ($Al_2O_3$) having additives of compounds of the alkaline metals group, the alkaline earths group, the IV B subgroup or the lanthanides group.

7 Claims, 1 Drawing Sheet

FOREIGN PATENT DOCUMENTS

| | | |
|---|---|---|
| DE | 102 56 476 | 7/2003 |
| EP | 0 159 905 | 10/1985 |
| EP | 311513 | 4/1989 |
| EP | 1 215 488 | 6/2002 |
| JP | 61079155 | 4/1986 |
| JP | 63019549 | 1/1988 |
| JP | 02276956 | 11/1990 |
| JP | 7027739 | 1/1995 |
| JP | 2001 281210 | 10/2001 |
| JP | 2003232769 | 8/2003 |
| JP | 2002291519 | 1/2004 |
| WO | 01 73418 | 10/2001 |

* cited by examiner

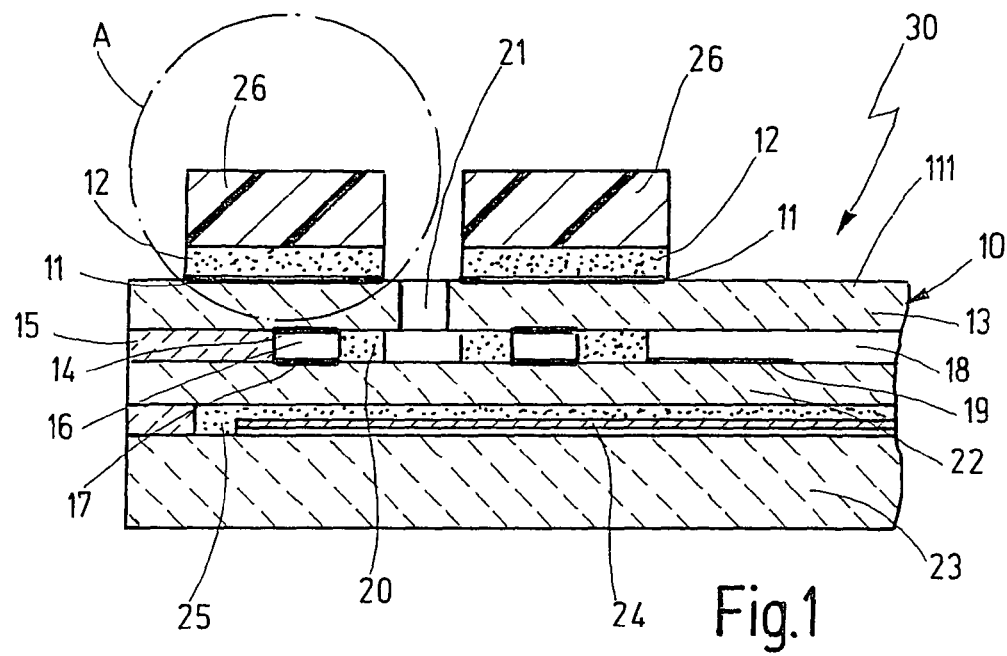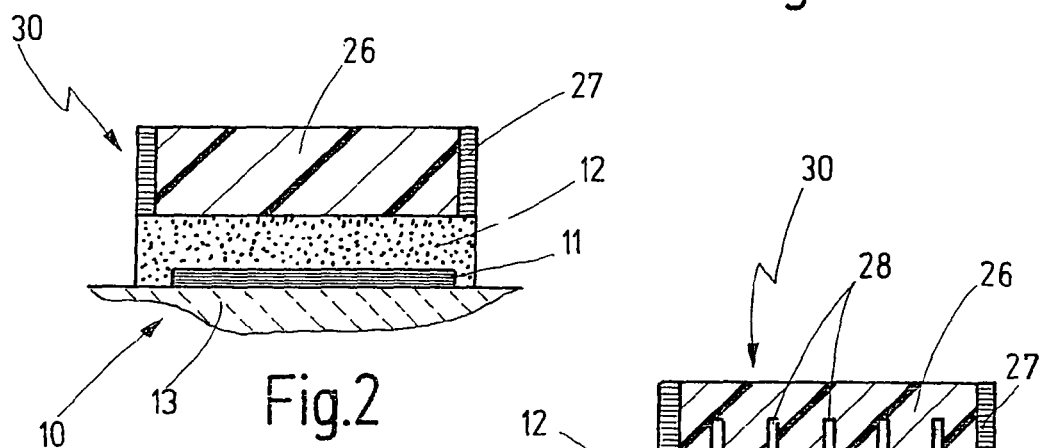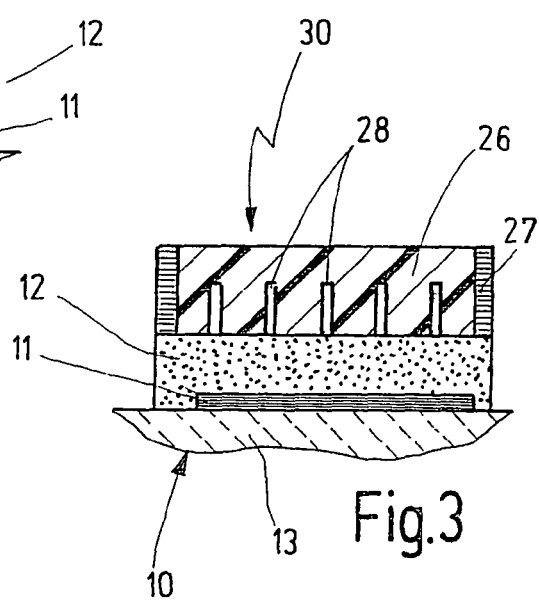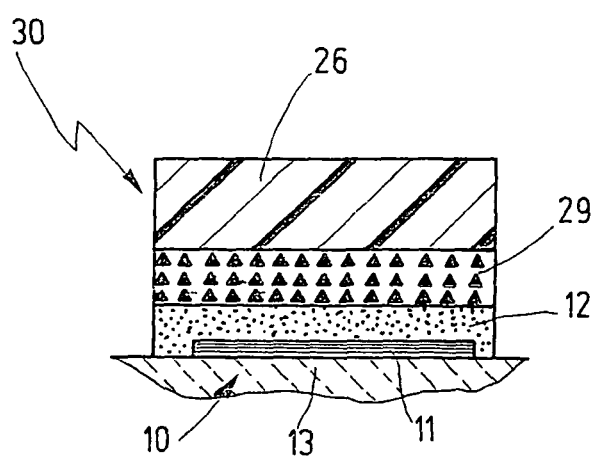

MEASURING SENSOR

FIELD OF THE INVENTION

The present invention is based on a sensing element for determining a physical property of a gas mixture, in particular for determining the oxygen concentration or the pollutant concentration in the exhaust gas of internal combustion engines.

BACKGROUND INFORMATION

In measuring sensors that are exposed to the exhaust gas of internal combustion engines, during driving operation, as a result of combustion residues and compounds contained in the exhaust gas, such as heavy metals, for example, lead, manganese, zinc, cadmium, magnesium, cerium, phosphorus, silicon, which originate with additives or residual pollutants in fuels, lubricating oils and gaskets of the internal combustion engine, deposits form on the sensor element which, in the long run, lead to glazing or clogging of the diffusion barrier and protective layers or to poisoning, that is, passivating of the catalytic activity, of the electrodes of the sensor element. The so-called contamination of the measuring sensor interferes with the function of the sensor element, since the electrodes preferably made up of platinum or platinum alloys lose their catalytic function.

In order to counter the so-called probe contamination due to lead residues, in one known measuring sensor of this type, (European Patent No. 0 159 905) the outer element of the sensor element is coated with a protective lining made up of a heat-resistant metal oxide, in which the lead-trapping, stable metals from the group platinum, ruthenium, paddaium, nickel, gold and alloys of the same are uniformly distributed.

SUMMARY OF THE INVENTION

The measuring sensor according to the present invention has the advantage that the novel protective layer extremely effectively prevents a "contamination" of the electrodes of the measuring sensor by silicon and phosphorus compounds as well as other particulate and gaseous harmful components in the measured gas, and may be manufactured cost-effectively from a production technology point of view. Because of its extreme porosity, the protective layer is able to be applied in great layer thickness, for instance, greater than 250 μm, which increases its effectiveness against contaminants, without the functional properties of the sensor element being impaired. The added solid in the protective layer may be introduced, for instance, as oxides, carbonates, acetates or nitrates of Ca, Al, La, Mg, Li, Ti, Zr. the measuring sensor according to the present invention may be designed as a finger probe or as a planar probe.

The method according to the present invention, for producing the protective layer on the sensor element of the present invention, has the advantage that the viscosity and the solid content of the flowable substance (slip) or spreadable, dough-like substance (paste) that are prepared in a water-based manner, may be optimized for the respectively selected method of application. As an inorganic binding agent, aluminum nitrate or an aluminum hydroxide gel are preferably added, and as organic binding agent preferably water-soluble polymers, such as PVP (polyvinylpyrolidon), hydroxyethylcellulose, tylose or Zaponlack, or water-dispersable polymers, such as polyvinyl alcohols (PVA) or polyvinyl acetates (PVAe) By selection of the method of application as well as the drying profile and burn-off profile, one may determine the desired layer thickness, layer porosity, layer adhesion and the layer stability of the protective layer.

The adhesion of the protective layer to the sensor element, and the durability of the protective layer may, in principle, be improved by a high burn-off temperature during the production method. It is true that, in this context, one must put up with a loss in activity of the protective layer. In order to achieve an advantageously great layer adhesion at a low baking temperature, which does not effect any impairing of the protective function of the protective layer, the surface of the sensor element is appropriately prepared before the application of the protective layer, according to additional embodiments of the method according to the present invention.

According to one advantageous specific embodiment of the present invention, the sensor element is produced having a surrounding frame on the protective lining and is sintered, and the substance is printed in the frame, such as in a silk-screen printing method, painted in or dripped in. The frame is preferably made of desnsely sintering zirconium oxide ($ZrO_2$).

According to one advantageous specific embodiment of the present invention, the sensor element, in addition to the surrounding frame, is produced to have columns that project from the surface of the protective lining inside the frame, and is sintered. In this context, the columns are preferably made of the same material as the protective lining. The columns bring about a greater stability as well as a mechanical anchoring of the protective layer on the protective lining of the sensor element.

According to an alternative specific embodiment of the present invention, the sensor element is made having a very porous adhesive layer that covers the protective lining and is sintered, and the substance is printed onto the adhesive layer, painted on, rolled on or dripped on. As the material for the very porous protective layer, preferably zirconium oxide ($ZrO_2$) is used, having a substantially higher proportion of aluminum oxide ($Al_2O_3$) than the protective lining and a higher proportion of a pore-forming material than the protective lining. When the protective layer is applied onto the adhesive layer, because of the great porosity of the adhesive layer, the protective layer penetrates into it and is firmly anchored mechanically to it by the subsequent drying and burn-out process and thereby also to the sensor element.

BRIEF DESCRIPTION OF THE DRAWINGS

FIG. 1 shows, sectionally, a longitudinal section of a sensor element of a measuring sensor.

FIGS. 2 to 4 show in each case an enlarged representation of cutout A in FIG. 1, having an exemplary embodiment for the pretreatment of the electrode protective lining in the measuring sensor according to FIG. 1.

DETAILED DESCRIPTION

Sensor element 30, shown in FIG. 1 sectionally schematically in longitudinal section for a measuring sensor developed, for example, as a planar broadband lambda probe for determining the oxygen concentration in the exhaust gas of internal combustion engines, is known as to construction and mode of operation, and is described in detail, for example, in German Patent No. 199 41 051. It has a ceramic element 10 made of a composite foil, on whose surface there is situated an outer electrode 11, which, in turn, is covered by a porous protective lining 12. Porous protective lining 12 is made of a zirconium oxide ($ZrO_2$) that has a low proportion of aluminum oxide ($Al_2O_3$). Outer electrode 11 is printed onto a first solid electrolyte layer 13, developed as a foil, made of yttrium-stabilized zirconium oxide ($ZrO_2$), and is connected to a printed circuit trace 111 that runs on the surface of solid electrolyte layer 13, for applying a voltage potential. On the lower side of solid electrolyte layer 13, an inner electrode 14 is printed on, lying opposite outer electrode 11. Both electrodes 11, 14 are made of platinum or a platinum alloy. Onto the lower side of first solid electrolyte layer 13 a second solid electrolyte layer 15, also designed as a foil, is printed on, using silk-screen printing of a paste-like ceramic material. In this second solid electrolyte layer 15 are formed, in a known manner, a measuring gas chamber 16, in which inner electrode 14 is positioned together with a measuring electrode 17, and a reference gas channel 18 in which a reference gas electrode 19 is situated. Reference gas channel 18 is subjected to a reference gas, such as environmental air, while measured gas chamber 16 is able to be exposed to the exhaust gas of the internal combustion engine via a diffusion barrier 20 and a bore 21 that is inserted into first solid electrolyte layer 13 and connected upstream of diffusion barrier 20. Measuring electrode 17 and reference electrode 19 as well as diffusion barrier 20 are printed onto a third solid electrolyte layer 22, which is also developed as a ceramic foil. Third solid electrolyte layer 22 is laminated together with a substrate 23, which may also be made up of a solid electrolyte. On the surface of substrate 23 that faces third solid electrolyte layer 22, there is a resistance heater 24 which is embedded in an insulation 25 made, for example, of aluminum oxide ($Al_2O_3$). Sensor element 30, thus constructed, is inserted into a housing of the measuring sensor in a gas-tight manner, and is connected via connecting lines to a connecting plug, so as to connect a control unit. The complete construction of the measuring sensor having the sensor element integrated into the housing is described in German Patent No. 197 41 203.

In order to prevent a "contamination" of sensor element 30 by residues contained in the exhaust gas and contaminated particulate or gaseous components, especially silicon compounds and phosphorus compounds, the sensor element is covered with a protective layer 26 which covers the porous protective lining 12 and, just as outer electrode 11 and porous protective lining 12, is left open in the area of bore 21 in first solid electrolyte layer 13. Protective layer 26 is made up of highly active γ- or δ-aluminum oxide ($Al_2O_3$) having additions of compounds of the alkaline metal groups, alkaline earth metal groups, IV B subgroup or lanthanide group, arid has great porosity and a large layer thickness, such as >250 μm. The additives are oxides, carbonates, acetates or nitrates of the elements named, such as lithium oxide.

Protective layer 26 on sensor element 30 of the measuring sensor is produced as follows:

The named components of protective layer 26, that is, aluminum oxide as a fine-particle, voluminous powder, and the additives, such as an alkaline earth oxide, are prepared with components of an organic and inorganic binding agent and a pore-forming substance in a water-based manner to form a pourable substance (a slip) or a paintable, dough-like substance (a paste). The viscosity (500-6000 mPas) and the solid matter content (35 wt.-% or less) of the substance is adapted to the type of the subsequent application method or the desired layer thickness of protective layer 26. The substance thus prepared is applied to protective lining 12 of sensor element 30. The application may be undertaken by dipping, rolling spraying, painting, dripping or printing. In the case of a finger-shaped sensor element, one has advantageously available the dipping, rolling or spraying method, and in the case of a planar sensor element 30, as shown in FIG. 1, the dipping, painting, dripping or printing method is available. After the substance is applied, sensor element 30 is subjected to a temperature between 20° C. (room temperature) and 180° C., whereby the applied substance dries. After that, sensor element 30 is subjected to a temperature between 450° C. and 1150° C., whereby the binding agent components and the pore-forming components burn off, and protective layer 26 sinters onto protective lining 12. The choice of application method, and the selected drying profile and burning-off profile are determinants for the layer thickness, the layer porosity and the layer adhesion and layer stability of protective layer 26 thus produced.

In principle, the layer adhesion may be improved by raising the baking temperature, in connection with which, however, one must be put up with a loss in activity of protective layer 26. In order to achieve a strong layer adhesion at an acceptable baking temperature, which does not lead to an impairment of the effectiveness of protective layer 26, before applying the substance prepared as described above to sensor element 30, the surface of protective lining 26 is suitably prepared.

In the section of sensor element 30 shown in FIG. 2, sensor element 30 is produced having a surrounding frame 27, which is preferably made up of a densely sintered zirconium oxide paste, and is sintered. Thereafter, the substance prepared as described above for protective layer 26 is then imprinted, painted or dripped into frame 27, and sensor element 30 is then treated as was described.

In the exemplary embodiment of sensor element 30 shown in FIG. 3, sensor element 30 is additionally produced having pillars 28 that extend from the surface of protective lining 12, within frame 27, and is sintered. Pillars 28 are made of the same material as protective lining 12. Now, again, the substance is imprinted, painted or dripped into frame 27, and then sensor element 30 is treated as was described.

In the exemplary embodiment of sensor element 30 shown in FIG. 4, sensor element 30 is additionally produced having an adhesive layer 29 that is applied to porous protective lining 12, and is sintered. Adhesive layer 29, in the same way as porous protective lining 12, is made up of zirconium oxide ($ZrO_2$) having proportions of aluminum oxide ($Al_2O_3$) and a pore-forming material proportion, however, the pore-forming material proportion being substantially increased and the aluminum oxide proportion being dimensioned greater. Because of the increased proportion of pore-forming material, finished sintered adhesion layer 29 is porous. On this porous adhesion layer, the substance for protective layer 26, that was prepared as described above, is printed on, painted on or dripped on, and then sensor element 30 is treated as described above. During the application of the substance onto adhesive layer 29, the substance penetrates porous adhesive layer 29, and protective layer 26 is mechanically firmly anchored in adhesive layer 29 during drying and sintering.

The application of protective layer 26, according to the present invention, is not limited to a planar sensor element 30 as shown in FIG. 1. It may be applied in the same way in the case of so-called finger probes, which are known, for instance, as stoichiometric or Nernst lambda probes.

What is claimed is:

1. A measuring sensor for determining a physical property of a measured gas, comprising:
   a sensor element capable of being exposed to the measured gas, the sensor element includes a ceramic element made of solid electrolyte layers, an outer electrode situated on a surface of the ceramic element, and a porous protective lining coating the outer electrode;
   a protective layer at least partially coating the sensor element, the protective layer protecting against a harmful component in the measured gas, the protective layer covering the porous protective lining, wherein the protective layer includes one of highly active γ-aluminum oxide ($Al_2O_3$) and highly active δ-aluminum oxide ($Al_2O_3$), the aluminum oxides having additives of one of the alkaline metals group, the alkaline earth group, the IV B subgroup, and the lanthanides group, wherein a material of the protective lining includes zirconium oxide ($ZrO_2$) having a small proportion of aluminum oxide ($Al_2O_3$), and wherein the protective layer has a substantially higher proportion of aluminum oxide than the protective lining; and a porous adhesive layer covering the protective lining, wherein a material of the adhesive layer includes zirconium oxide ($ZrO_2$) having a proportion of aluminum oxide ($Al_2O_3$).

2. The measuring sensor as recited in claim 1, wherein the measuring sensor is for determining one of an oxygen concentration and a contaminant concentration in an exhaust gas of an internal combustion engine.

3. The measuring sensor as recited in claim 1, wherein the additives are one of oxides, carbonates, acetates, and nitrates of elements of the one of the alkaline metals group, the alkaline earth group, the IV B subgroup, and the lanthanides group.

4. The measuring sensor as recited in claim 1, wherein the protective layer is extremely porous and has a great layer thickness.

5. The measuring sensor as recited in claim 1, wherein a thickness of the protective layer is greater than 250 μm.

6. The measuring sensor as recited in claim 1, wherein a porosity of the porous adhesive layer is substantially greater than that of the protective lining.

7. The measuring sensor as recited in claim 1, wherein the porous adhesive layer is situated below the protective layer.

* * * * *